United States Patent
Yamada (10) Patent No.: US 8,737,569 B2
(45) Date of Patent: May 27, 2014

(54) RADIOGRAPHY CONTROL APPARATUS AND RADIOGRAPHY CONTROL METHOD

(75) Inventor: Naoki Yamada, Soka (JP)

(73) Assignee: Canon Kabushiki Kaisha, Tokyo (JP)

( * ) Notice: Subject to any disclaimer, the term of this patent is extended or adjusted under 35 U.S.C. 154(b) by 141 days.

(21) Appl. No.: 13/218,110

(22) Filed: Aug. 25, 2011

(65) Prior Publication Data

US 2011/0305323 A1  Dec. 15, 2011

Related U.S. Application Data

(63) Continuation of application No. 12/479,808, filed on Jun. 7, 2009, now Pat. No. 8,027,432.

(30) Foreign Application Priority Data

Jun. 10, 2008  (JP) .................................. 2008-151821

(51) Int. Cl.
*H05G 1/58* (2006.01)

(52) U.S. Cl.
USPC ........................................................ 378/116

(58) Field of Classification Search
USPC ............................ 378/62, 116, 162, 165, 207
See application file for complete search history.

(56) References Cited

U.S. PATENT DOCUMENTS

| 8,027,432 B2 * | 9/2011 | Yamada | ........................ 378/116 |
| 2003/0210762 A1 * | 11/2003 | Spahn | ............................. 378/62 |

FOREIGN PATENT DOCUMENTS

| JP | 63-082627 A | 4/1988 |
| JP | 2002-369084 A | 12/2002 |
| JP | 2003-194949 A | 7/2003 |
| JP | 2004-023654 A | 1/2004 |
| JP | 2007-068014 A | 3/2007 |
| JP | 2007-330617 A | 12/2007 |

* cited by examiner

*Primary Examiner* — Irakli Kiknadze
(74) *Attorney, Agent, or Firm* — Canon USA, Inc. IP Division (57) ABSTRACT

A radiography control apparatus includes an acquisition unit configured to acquire data of image-capturing mode and a change unit configured to change the number of times a correction image is captured, the correction image being used to correct a radiographic image in accordance with the acquired image-capturing-mode data.

27 Claims, 9 Drawing Sheets

RADIOGRAPHY CONTROL APPARATUS AND RADIOGRAPHY CONTROL METHOD

CROSS-REFERENCE TO RELATED APPLICATIONS

This application claims the benefit of U.S. application Ser. No. 12/479,808, filed Jun. 7, 2009 and Japanese Patent Application No. 2008-151821 filed on Jun. 10, 2008, which is hereby incorporated by reference herein in their entireties.

BACKGROUND OF THE INVENTION

1. Field of the Invention

The present invention relates to an apparatus and a method that are provided to control a radiographic apparatus configured to capture a radiographic image.

2. Description of the Related Art

Generally, radiographic imaging apparatuses including an image-pickup unit configured to pick up a radiographic image has been used to perform medical radiography, industrial nondestructive radiography, and so forth.

For using the radiographic imaging apparatus while maintaining the initial performance capabilities thereof, the characteristics of the image-pickup unit should be calibrated, where the characteristics are changed over time. Usually, a calibration operation has been performed by a user (e.g., a radiologic technologist working in a hospital). Further, the frequency of performing the calibration operation has been determined under an operation rule established for each facility under present circumstances. That is to say, the calibration operation has been performed at the opening time every day, or once every half a year and/or year under the operation rule established for the facility.

In the following case, a correction image used to correct gain variation is acquired, as an exemplary calibration operation. For acquiring the above-described correction image, the user arranges the radiation source (an X-ray tube) and the image-pickup unit at appropriate positions in the first place. When the radiation source and the image-pickup unit are arranged at the appropriate positions, the entire image-pickup unit is irradiated with a radiation emitted from the radiation source (the X-ray tube), for example. Next, the user sets a tube voltage and/or a tube current related to the occurrence of radiation to an appropriate value, and actually irradiates the image-pickup unit with radiation. At that time, the irradiation is performed without placing any object (subject).

The image of the dose of radiation detected during the above-described irradiation is picked up as image data and subjected to image processing. Consequently, the correction image used to correct the gain variation is acquired.

Here, an image captured without placing any object (subject) is generally referred to as a gain image and/or a white image (hereinafter referred to as the gain image).

A calibration method used for the above-described image-pickup unit is disclosed in Japanese Patent Laid-Open No. 2001-351091. Namely, when capturing and acquiring the gain image without placing any object (subject) at the calibration time, a plurality of the gain images (approximately four gain images in most instances) is acquired, so as to reduce random noises included in the gain images. Namely, the plurality of gain images have been acquired and averaged so that the random noises included in the gain images are reduced. The reduction of the random noises, which is attained by the averaging, should be performed to generate a correction image with high precision.

The above-described correction image is used as a correction image used to perform the gain correction when the image of an object (subject) is captured under normal conditions, for example. More specifically, the captured images are omitted by using the correction image, so as to correct the gain variation between the captured images. Therefore, when the gain correction is performed for a captured image by using a correction image with low precision (including many random noises), artifacts are left in the corrected captured image. In that case, therefore, it becomes difficult to obtain an appropriate captured image. Accordingly, a correction image with high precision should be generated at the calibration time.

Thus, according to known technologies of generating the correction image, the random noises have been reduced by acquiring and averaging a predetermined number of captured gain images. However, for generating a correction image with higher precision, consideration should be given to image-capturing mode used at the calibration time (e.g., the radiation dose), because the amount of random noise included in the gain image varies with image-capturing modes. According to the known technologies, therefore, the number of times the image capturing is performed becomes unnecessarily large, for acquiring the correction image, so that the life of the radiographic apparatus is often reduced. Further, the number of times the image capturing is performed often becomes so small that appropriate correction precision is obtained with difficulty.

Further, the number of times the image capturing is performed to obtain four gain images becomes four or around under normal conditions. However, the time number four is often manually set by a user at the calibration time. However, the user does not know whether the time number four is sufficient for reducing the random noises included in the gain image, and what should be used as a guide to set the time number. In the past, therefore, the time number has been determined and set under empirical rule established by the user. Accordingly, the present invention has been achieved to set the number of times the image capturing is performed, the time number being appropriate to perform calibration for the radiographic apparatus.

SUMMARY OF THE INVENTION

The present invention has been made in consideration of the above situation, and has as its object to set the number of times image capturing is performed, the time number being appropriate for performing calibration for a radiographic apparatus.

According to the present invention, the foregoing object is attained by providing a radiography control apparatus. The radiography control apparatus includes an acquisition unit configured to acquire data of image-capturing mode, and a change unit configured to change the number of times a correction image is captured, the correction image being used to correct a radiographic image in accordance with the acquired image-capturing-mode data.

Other features and aspects of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Numerous embodiments of the present invention will be described in detail in accordance with the accompanying drawings.

Hereinafter, a first embodiment of the present invention will be described with reference to the attached drawings.

Figure 1:
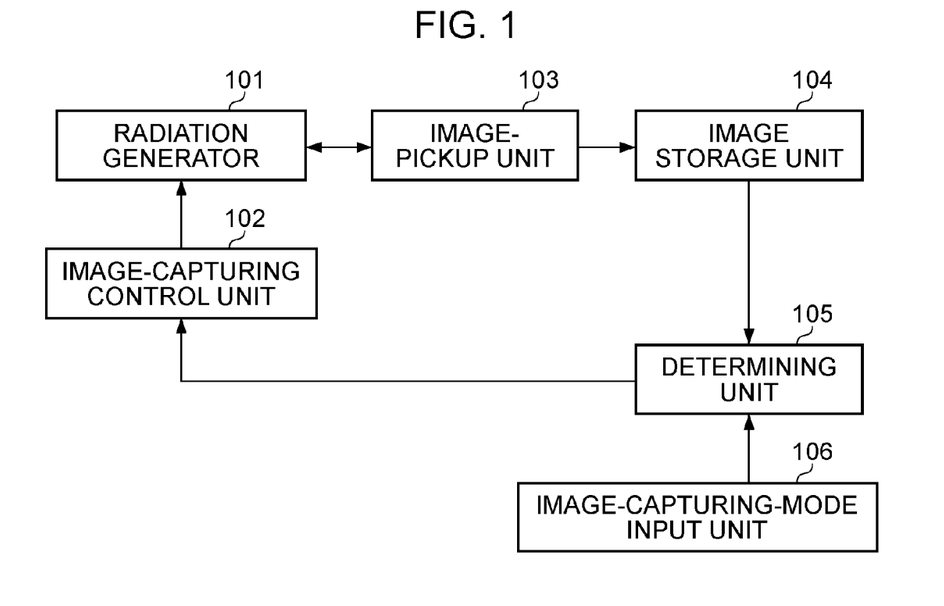
FIG. 1 is an exemplary functional configuration diagram of a radiographic apparatus according to a first embodiment of the present invention.

FIG. 1 is a functional configuration diagram of a radiographic apparatus and a radiography control apparatus according to the first embodiment. The configuration of each of the above-described apparatuses will be described below.

A radiation generator 101 includes a radiation source (an X-ray tube) and a high-voltage generator configured to generate a high voltage used to perform radiation irradiation.

An image-capturing control unit 102 is configured to control the time when the radiation generator 101 performs the radiation irradiation. That is to say, the image-capturing control unit 102 controls radiography. Therefore, the radiation generator 101 starts and stops the radiation irradiation based on an instruction transmitted from the image-capturing control unit 102. The image-capturing control unit 102 functions as a control unit configured to control the radiation generator 101.

An image-pickup unit 103 is configured to pick up a radiation image. The image-pickup unit 103 includes, for example, a radiation-detecting sensor that can detect a radiation. Therefore, a radiation applied from the radiation generator 101 is converted into a video signal indicating a radiographic image through the image-pickup unit 103.

An image storage unit 104 is configured to store data of a radiographic image generated based on the video signal transmitted from the image-pickup unit 103. The image storage unit 104 includes a recording medium including a hard disk configured to store image data, a semiconductor device, and so forth.

A determining unit 105 is configured to determine the number of times a correction image is captured, the correction image being used to perform a calibration for a captured image (the number of captured images), and notify the image-capturing unit 102 of the desired number of times the correction image is captured. The determining unit 105 includes a random access memory (RAM) storing a program used to perform determining processing, a central processing unit (CPU) configured to execute the program, and so forth. The determining unit 105 functions as a change unit configured to change the number of times the correction image is captured.

An image-capturing-mode input unit 106 is configured to input data of image-capturing mode used to determine the number of times the correction image is captured, the correction image being used to perform the calibration. As is the case with the input devices of widely used personal computers (PCs), the image-capturing-mode input unit 106 is provided with input devices including a keyboard, a mouse, and so forth, and functions as an acquisition unit configured to acquire data of the image-capturing mode. The image-capturing-mode data input through the image-capturing-mode input unit 106 is transmitted to the determining unit 105. The determining unit 105 determines the number of times the correction image is captured based on the transmitted data of conditions, the correction image being used to perform the calibration for the captured image. Further, the determining unit 105 notifies the image-capturing control unit 102 of the determined number.

The image-capturing control unit 102 controls the radiation generator 101 starting and/or stopping the radiation irradiation so that the radiography is performed the notified number of times the correction image is captured, the correction image being used to perform the calibration. Here, part of the functions illustrated in the functional configuration diagram shown in FIG. 1 can be replaced with a widely used PC and a widely used computer program, or provided as a computer readable recording medium. Next, example condition data input through the image-capturing-mode input unit 106 and an example determination made by the determining unit 105 will be described.

According to the above-described embodiment, the determining unit 105 changes a predetermined number of times the correction image used for the calibration is captured based on the condition data input through the image-capturing-mode input unit 106. The predetermined number of times the correction image used for the calibration is captured is determined to be four. The time number four has been widely set as the number of correction images used for a static image. The following seven image-capturing modes are determined to be image-capturing modes of which data is input through the image-capturing-mode input unit 106. However, without being limited to the above-described seven image-capturing modes, other image-capturing modes and/or the combination thereof can be used, which constitutes another embodiment of the present invention.

(Image-Capturing Mode 1)

Image-capturing mode 1 indicates the dose of radiation used to perform radiography. Generally, as the dose of radiation used to perform the radiography grows, so does the amount of occurring random noise. However, since the ratio of random noise to the radiation dose decreases in relative terms, the number of times the correction image is captured decreases, the correction image being used to perform the calibration. Therefore, when the radiation dose of which data is input through the image-capturing-mode input unit 106 falls above a predetermined range, the determining unit 105 decreases the predetermined number of times the correction image used to perform the calibration is captured.

On the contrary, when the radiation dose of which data is input through the image-capturing-mode input unit 106 falls below the predetermined range, the determining unit 105 increases the predetermined number of times the correction image used to perform the calibration is captured. In the above-described embodiment, the number of times the correction image is captured is inversely proportional to the radiation dose.

Therefore, when performing image capturing by using radiation of which dose is twice as much as that of radiation used for performing ordinary static-image photography, for example, the number of correction images becomes two, which is half of the predetermined number four. On the contrary, when performing the image capturing by using radiation of which dose is half of that of radiation used for performing the ordinary static-image photography, the number of the correction images becomes eight, which is twice the predetermined number four.

(Image-Capturing Mode 2)

Image-capturing mode 2 indicates the types of radiography, that is, static-image capturing, moving-image capturing, and so forth. According to the above-described embodiment, either of the static-image capturing and the moving-image capturing is selected, as the radiography type. When the static-image capturing is selected as the radiography type, the dose of radiation used for a single radiographic image becomes larger than that of radiation used for capturing a moving image. Therefore, the number of times the correction image used to perform the calibration is captured is decreased. Therefore, when the image-capturing-mode input unit 106 inputs data of the static-image capturing, as the condition of setting the radiography type, the determining unit 105 does not change the predetermined number of times the correction image is captured, the correction image being used to perform the calibration.

On the contrary, when the image-capturing-mode input unit 106 inputs data of the moving-image capturing, as the condition of setting the radiography type, the determining unit 105 increases the predetermined number of times the correction image is captured, the correction image being used to perform the calibration. Generally, since the dose of radiation used for a single moving image is about half of that of radiation used for a single static image, the number of the correction images is set to eight, which is twice the predetermined number four. However, since the number of correction images that are used for a moving image has been generally expected to be ten, the number of the correction images that are used for the moving image may be determined to be ten.

(Image-Capturing Mode 3)

Image-capturing mode 3 indicates the types of correction images. The correction-image types denote, for example, a correction image used for capturing a static image, a correction image used for capturing a moving image, and so forth. In the above-described embodiment, either of the correction image used for capturing the static image and that used for capturing the moving image is selected, as the correction-image type. When the correction-image type indicates the correction image used for capturing the static image, the amount of random noise occurring in a static image for correction becomes smaller than that of random noise occurring in a moving image. Therefore, the number of times the correction image used to perform the calibration is captured is decreased.

Therefore, when the correction-image-type data input through the image-capturing-mode input unit 106 indicates the correction image used to perform the static-image capturing, the determining unit 105 does not change the predetermined number of times the correction image is captured, the correction image being used to perform the calibration. On the contrary, when the correction-image-type data input through the image-capturing-mode input unit 106 indicates the correction image used to perform the moving-image capturing, the determining unit 105 increases the predetermined number of times the correction image is captured, as is the case with the image-capturing mode 2, the correction image being used to perform the calibration.

(Image-Capturing Mode 4)

Image-capturing mode 4 indicates frame rates that are used to perform the radiography. As the frame rate used to perform the radiography decreases, the dose of radiation used for a single radiographic image increases so that the number of times the correction image is captured decreases, the correction image being used to perform the calibration. Commonly used frame rates are expressed as 60 fps, 30 fps, 15 fps, 7.5 fps, 5 fps, 1 fps, and so forth. In the above-described embodiment, the frame rates 60 fps and 30 fps are determined to be high frame rates, the frame rates 15 fps and 7.5 fps are determined to be medium frame rates, and the frame rates 5 fps and 1 fps are determined to be low frame rates. When data of the high frame rate is input through the image-capturing-mode input unit 106, the determining unit 105 increases the predetermined number of times the correction image is captured, the correction image being used to perform the calibration. When data of the medium frame rate is input through the image-capturing-mode input unit 106, the determining unit 105 does not change the predetermined number of times the correction image is captured. Further, when data of the low frame rate is input through the image-capturing-mode input unit 106, the determining unit 105 decreases the predetermined number of times the correction image is captured.

(Image-Capturing Mode 5)

Image-capturing mode 5 indicates whether addition reading should be performed. When performing the radiography, the addition reading is often performed, so as to perform processing with speed. When performing ordinary reading, a single pixel of image data is detected from a single pixel included in the image-pickup unit 103. When the addition reading is performed, the single pixel of the image data is detected from 2×2 pixels of the image-pickup unit 103. Generally, data can be read with high speed by performing the addition reading. However, the image data acquired through the addition reading is rough. When performing the addition reading, the dose of radiation is often determined to be low and the number of times the correction image used to perform the calibration is captured is increased.

Therefore, when data indicating that the addition reading should be performed is input through the image-capturing-mode input unit 106, the determining unit 105 increases the predetermined number of times the correction image used to perform the calibration is captured. Further, as the number of pixels used to perform the addition reading grows, as in the case where 4- by 4-pixel reading, 8- by 8-pixel reading, and 16- by 16-pixel reading are performed in that order, the number of times the correction image used to perform the calibration is captured is increased. On the contrary, when data indicating that the addition reading should not be performed is input through the image-capturing-mode input unit 106, the determining unit 105 does not change the predetermined number of times the correction image used to perform the calibration is captured.

(Image-Capturing Mode 6)

Image-capturing mode 6 indicates whether a grid should be used. Generally, when the radiography is performed by using the grid, the dose of radiography reaching the image-pickup unit 103 is decreased. Therefore, the radiography dose is often determined to be high. Consequently, when data indicating that the grid should be used is input through the image-capturing-mode input unit 106, the determining unit 105 increases the predetermined number of times the correction image used to perform the calibration is captured. On the contrary, when data indicating that the grid should not be used is input through the image-capturing-mode input unit 106, the determining unit 105 does not change the predetermined number of times the correction image is captured.
(Image-Capturing Mode 7)

Image-capturing mode 7 indicates the condition of the distance between the radiation source and the image-pickup unit 103. Generally, as the distance between the radiation source and the image-pickup unit 103 is decreased, the dose of radiation reaching the image-pickup unit 103 is increased and the number of times the correction image used to perform the calibration is decreased.

Therefore, when the distance between the radiation source and the image-pickup unit 103, where data of the above-described distance is input through the image-capturing-mode input unit 106, is smaller than a predetermined distance, the determining unit 105 decreases the predetermined number of times the correction image used to perform the calibration is captured. On the contrary, when the distance between the radiation source and the image-pickup unit 103, where data of the above-described distance is input through the image-capturing-mode input unit 106, is larger than the predetermined distance, the determining unit 105 does not change the predetermined number of times the correction image used to perform the calibration is captured.

By changing the number of times the correction image is captured in accordance with the input image-capturing-mode data, the number of times the correction image used to make the correction can be determined appropriately. When the above-described predetermined number of correction images are acquired, the radiographic image can be corrected more appropriately than in the past.

In the above-described embodiment, the number of times the correction image used to make the correction is captured is changed based on the image-capturing mode of which data is input through the image-capturing-mode input unit 106. However, the above-described number may be changed based on the analysis of image data stored in the image-storage unit 104 in addition to the input image-capturing-mode data.

In the first embodiment, the number of times the correction image used to make the correction is captured is changed based on the input image-capturing-mode data. In a second embodiment of the present invention, the radiography is controlled based on whether a statistic calculated by analyzing the radiographic image and/or a comparison value calculated based on the statistic reaches the value of a target precision provided as a target value. In the above-described embodiment, the statistic denotes dispersion and/or a standard deviation calculated based on the distribution of the pixel values of the correction image. The dispersion and/or the standard deviation may indicate the amount of random noise occurring in the correction image. In the above-described embodiment, it can be determined that the target precision is attained when the calculated statistic and/or the calculated comparison value falls below the target precision value.

Figure 2:
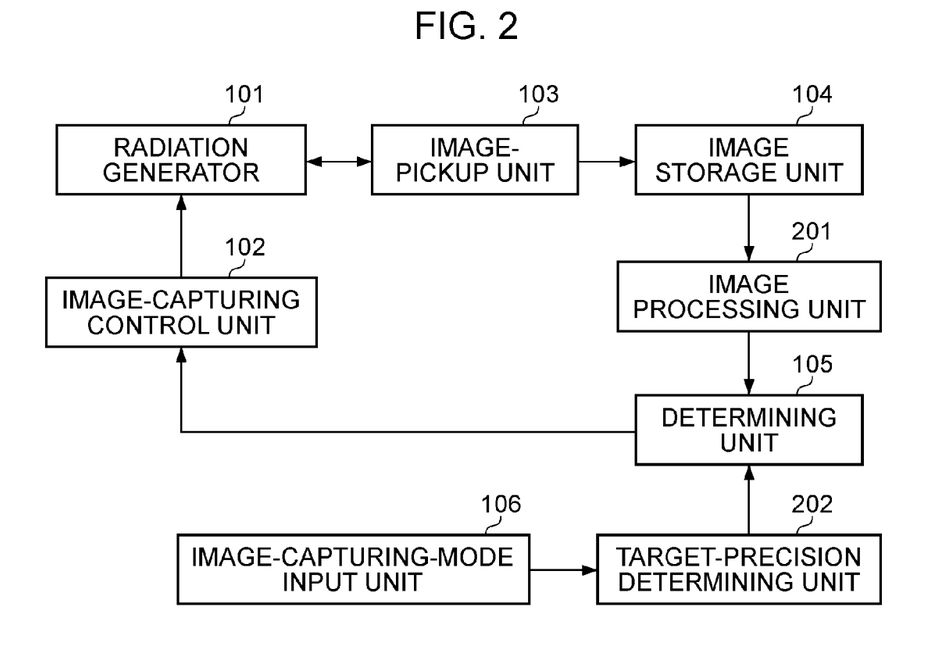
FIG. 2 is an exemplary functional configuration diagram of a radiographic apparatus according to a second embodiment of the present invention.

FIG. 2 is the functional configuration diagram of a radiographic apparatus according to the above-described embodiment. The difference between FIG. 2 and FIG. 1 showing the functional configuration of the first embodiment will be described below.

An image processing unit 201 is configured to perform image processing for a radiographic image of which data is stored in the image-storage unit 104. The image processing unit 201 performs image processing for the radiographic image, so as to calculate the statistic based on the dispersion, the standard deviation, and so forth of the radiographic image. The image-processing unit 201 includes a RAM storing a program provided to perform the image processing, a CPU executing the program provided to perform the image processing, and so forth.

A target-precision determining unit 202 is configured to determine an appropriate target precision based on the image-capturing-mode data input through the image-capturing-mode input unit 106. The target-precision determining unit 202 includes a RAM storing a program provided to determine the target precision, a CPU executing the program provided to determine the target precision, and so forth.

In the above-described embodiment, the target-precision determining unit 202 changes a predetermined target precision based on the image-capturing-mode data input through the image-capturing-mode input unit 106. The image-capturing-mode data input through the image-capturing-mode input unit 106 indicates the same seven image-capturing modes as those described in the first embodiment. However, the condition of the above-described embodiment is not limited to the seven image-capturing modes as is the case with the first embodiment. If the image-capturing mode of which data is input to the image-capturing input unit 106 indicates an increase in the radiation dose, the impact of the random noise is decreased in relative terms. Therefore, the target-precision determining unit 202 increases the predetermined target precision.

By increasing the target precision, the number of the correction images that are used to attain the target precision is decreased. On the contrary, if the image-capturing mode of which data is input to the image-capturing input unit 106 indicates a decrease in the radiation dose, the impact of the random noise is increased in relative terms. Therefore, the target-precision determining unit 202 decreases the predetermined target precision. When the target precision is decreased, a large number of the correction images should be provided to attain the target precision.

The determining unit 105 determines whether the value of the statistic calculated by the image processing unit 201 falls below that of the target precision determined by the target-precision determining unit 202. If the statistic value does not fall below the target precision value, it is determined that a sufficient number of the correction images are not acquired. Therefore, an instruction to perform radiography is transmitted to the image-capturing control unit 102. If the statistic value falls below the target precision value, it is determined that the sufficient number of the correction images are acquired. Therefore, the correction-image-acquisition processing is terminated without transmitting the radiography instruction to the image-capturing-control unit 102.

Thus, the functional configuration shown in FIG. 2 is different from that shown in FIG. 1. Here, part of the functions illustrated in the functional configuration diagram shown in FIG. 2 can be replaced with a widely used PC and a widely used computer program, and provided as a computer readable recording medium. Next, details of four determining processing procedures according to the above-described embodiment will be described.
(First Determining Method)

Figure 3:
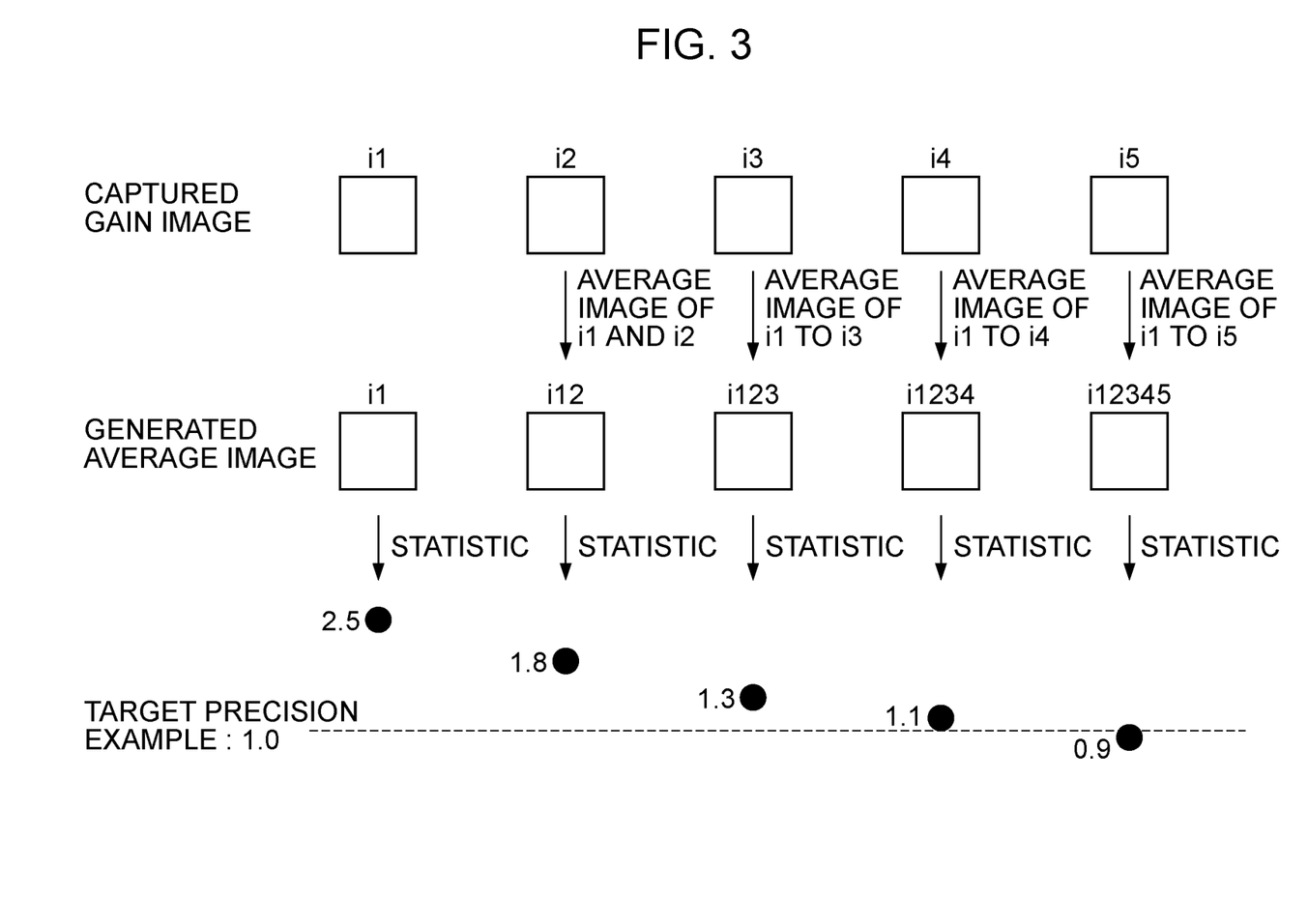
FIG. 3 shows a first determining method performed based on a target precision determined by a target-precision determining unit.

FIG. 3 shows the first determining method performed based on the target precision determined by the target-precision determining unit 202. In FIG. 3, the value of the target precision is set to 1.0, and the statistic of the average image of captured gain images is compared with the target precision.

The gain images are acquired by performing the radiography without placing any subject and are commonly used as the correction images.

As shown in FIG. 3, the statistic value is decreased as the number of times the gain image is captured is increased. When the fifth gain image is captured, the statistic value reaches the target-precision value. Thus, the gain image is repeatedly acquired until the statistic value reaches the target-precision value. Consequently, an appropriate number of the correction images can be captured and acquired.

Figure 4:
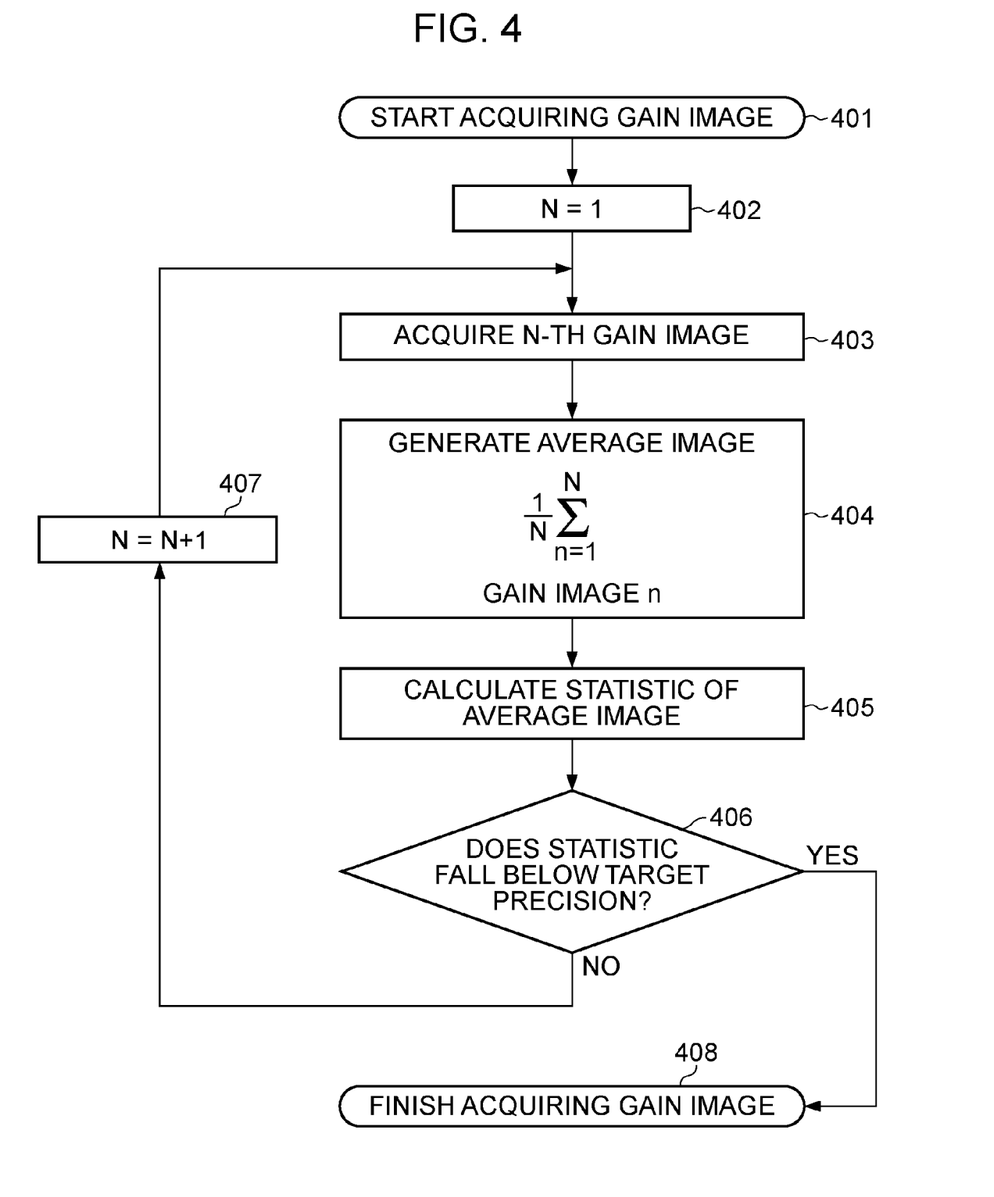
FIG. 4 is a flowchart of processing procedures performed to execute the first determining method.

FIG. 4 is a flowchart of processing procedures performed to attain the first determining method shown in FIG. 3. The details of the processing procedures will be described below.

At step S401, the radiographic apparatus starts acquiring the gain images upon receiving an instruction to acquire the correction images, the instruction being transmitted from a user.

At step S402, the determining unit 105 determines the value of the sign N to be one, where the sign N is a parameter representing the number of times the gain image is captured.

At step S403, the image-capturing-control unit 102 makes the radiation generator 101 emit radiation and acquires the N-th gain image. Data of the acquired N-th gain image is stored in the image storage unit 104 and the image processing unit 201 acquires the N-th-gain-image data stored in the image storage unit 104. For example, if the parameter N denotes one, a gain image i1 shown in FIG. 3 is acquired, and if the parameter N denotes two, a gain image i2 shown in FIG. 3 is acquired.

At step S404, the image processing unit 201 generates the average image of the gain images that are acquired at step S403. When the parameter N denotes one, the gain image i1 is determined to be the average image, since it is difficult to generate the average image.

At step S405, the statistic of the average image generated at step S404 is calculated. As described above, the statistic used in the above-described embodiment denotes the standard deviation and/or the dispersion.

At step S406, the determining unit 105 determines whether the value of the statistic calculated at step S405 falls below the target precision value. If it is determined that the statistic value does not fall below the target precision value, the processing advances to step S407, so as to acquire another gain image. If it is determined that the statistic value falls below the target precision value, it can be determined that a sufficient number of gain images to make the correction are acquired. Therefore, the processing advances to step S408.

At step S407, the determining unit 105 adds one to the parameter N representing the number of times the gain image is captured. After one is added to the parameter N, the processing advances to step S403 again so that the gain image is acquired.

At step S408, since it is determined that the sufficient number of gain images to make the correction are acquired at step S406, the radiographic apparatus stops acquiring the gain images.

As described above, the sufficient number of gain images to make the correction can be acquired by performing the processing procedures corresponding to steps S401 to S408.

(Second Determining Method)

Figure 5:
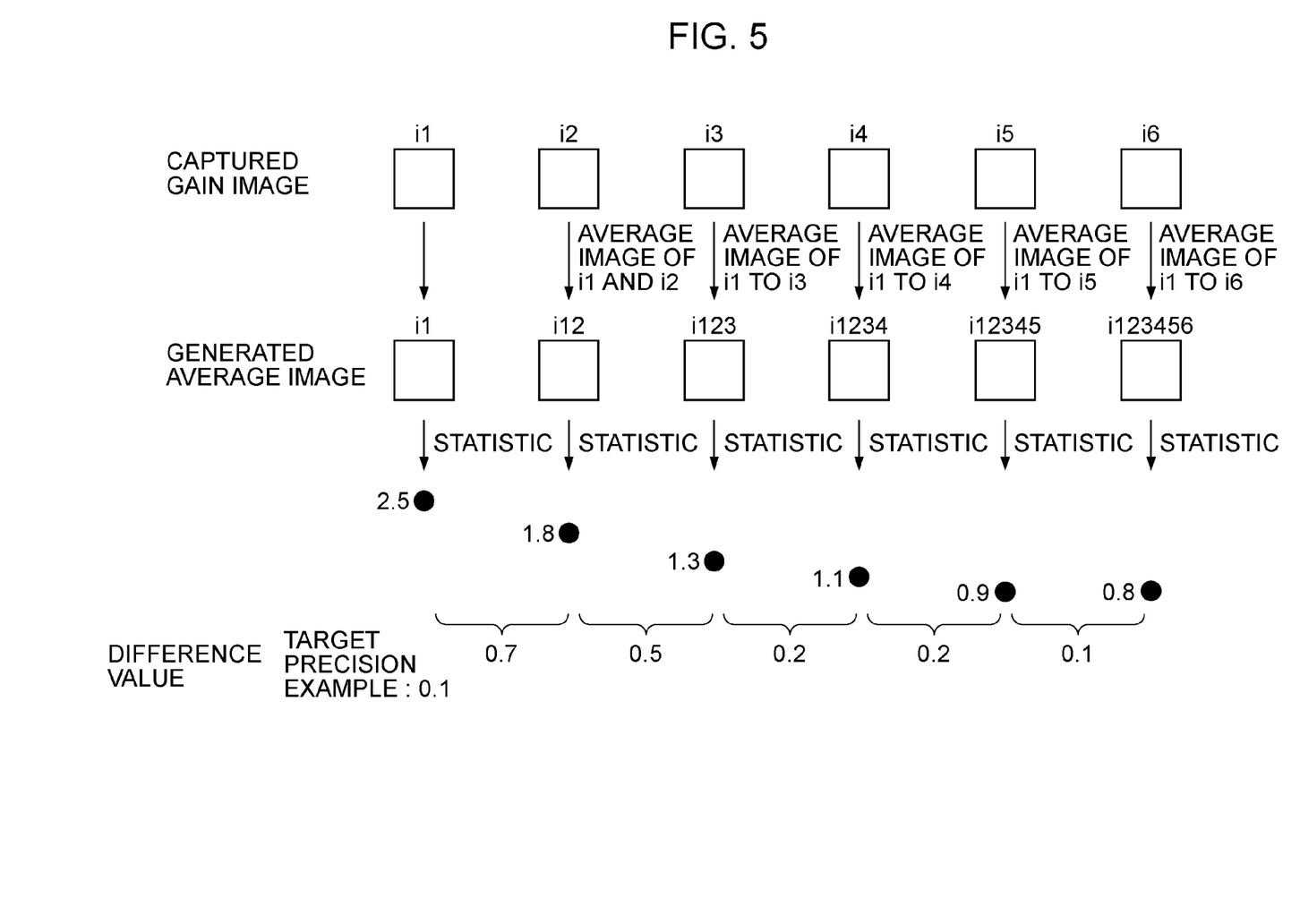
FIG. 5 shows a second determining method performed based on another target precision determined by the target-precision determining unit.

FIG. 5 shows the second determining method performed based on another target precision determined by the target-precision determining unit 202. In FIG. 5, the value of the target precision is set to 0.1, and the difference value of the statistic of the average image of the captured gain images is compared with the value of the target precision. As shown in FIG. 5, the difference value of the statistic is decreased as the number of times the gain image is captured is increased. When the sixth gain image is captured, the difference value of the statistic reaches the target precision value. Thus, the gain image is repeatedly acquired until the statistic value reaches the target-precision value. Consequently, the appropriate number of the correction images can be captured and acquired.

Figure 6:
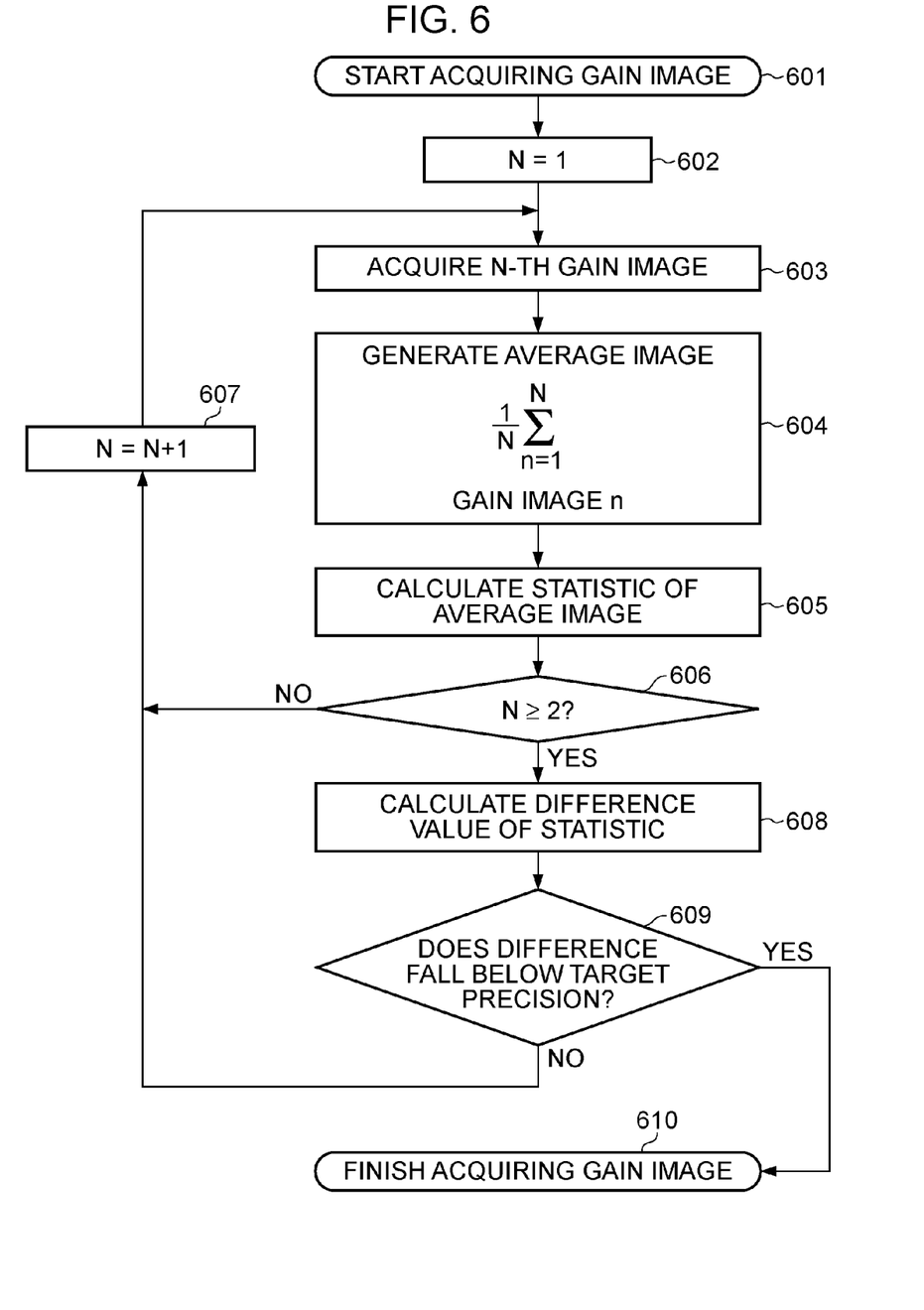
FIG. 6 is a flowchart of processing procedures performed to execute the second determining method.

FIG. 6 is a flowchart of processing procedures performed to attain the second determining method shown in FIG. 5. The details of the processing procedures will be described below. Here, the processing procedures corresponding to steps S601 to S605 of the second determining method are equivalent to those corresponding to steps S401 to S405 of the first determining method. Further, steps S607, S609, and S601 correspond to steps S407, S406, and S408, respectively. Hereinafter, therefore, the processing procedures corresponding to steps S606 and S608, which are different from the first determining method, will be described.

At step S606, the determining unit 105 determines whether the parameter N representing the number of times the image capturing is performed is equivalent to or greater than two. If the parameter N is equivalent to or greater than two, the processing advances to step S608 so that the difference value of the statistic is calculated. If the parameter N is not equivalent to or greater than two, it is difficult to calculate the difference value of the statistic. Therefore, the processing advances to step S607 so that another gain image is acquired.

At step S608, the image processing unit 201 calculates the difference in the statistic calculated at step S605. After the difference in the statistic is calculated, the processing advances to step S609 so that whether the value of the difference falls below the target precision value is determined.

As described above, the sufficient number of gain images to make the correction can be acquired by performing the processing procedures corresponding to steps S601 to S610.

(Third Determining Method)

Figure 7:
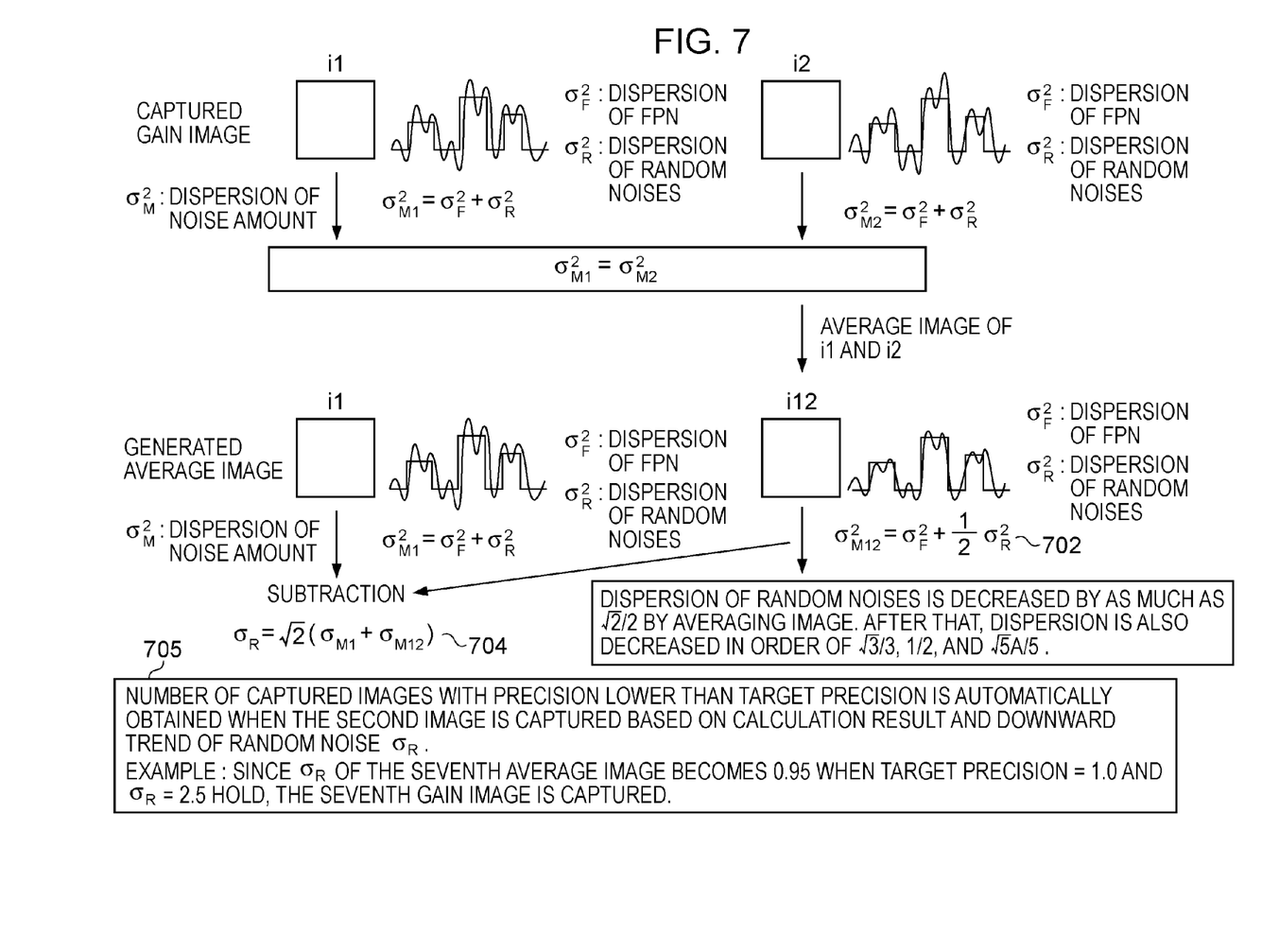
FIG. 7 shows a third determining method performed based on another target precision determined by the target-precision determining unit.

FIG. 7 shows the third determining method performed based on another target precision determined by the target-precision determining unit 202. The third determining method shown in FIG. 7 is provided to calculate the dispersion of the random noises, and calculates the number of times the image capturing is performed, the number being large enough to attain the target precision, when the random-noise dispersion is decreased in keeping with a predetermined downward trend. More specifically, the statistic of the gain image i1, and the statistic of the average image of the gain images i1 and i2 are calculated. When each of the statistics obtained through the third determining method is determined to be dispersion, the dispersion includes dispersion caused by the random noise and a fixed noise referred to as a fixed pattern noise (FPN). Generally, in the same image-capturing mode, the amount and the distribution of the dispersion of the FPNs (fixed noises) occurring in a predetermined image become constant. Likewise, the amount of the random noises occurring in the predetermined image becomes constant, even though the distribution of the random noises varies.

Through averaging processing, therefore, a dispersion caused by random noises occurring in the average image is half a dispersion caused by random noises occurring in the gain image i1 (702 shown in FIG. 7). Consequently, it becomes possible to calculate a dispersion caused by the random noises by calculating the difference between the dispersion of the gain image i1 and that of the average image of the gain images i1 and i2 (704 shown in FIG. 7).

If the dispersion caused by the random noises can be calculated, it becomes possible to calculate the number of times the image capturing is performed, the number being large enough to attain the target precision, when the random-noise dispersion is decreased in keeping with the predetermined downward trend. After reducing a square component, the decrease in the random noises caused by two gain images is expressed as $\sqrt{2}/2$. Hereinafter, as the number of the gain images increases in order of 3, 4, and 5, the random-noise amount decreases in order of $\sqrt{3}/3$, 1/2, and $\sqrt{5}A/5$. Therefore, it becomes possible to calculate the number of times the image capturing is performed, the number being large enough to attain the target precision.

Figure 8:
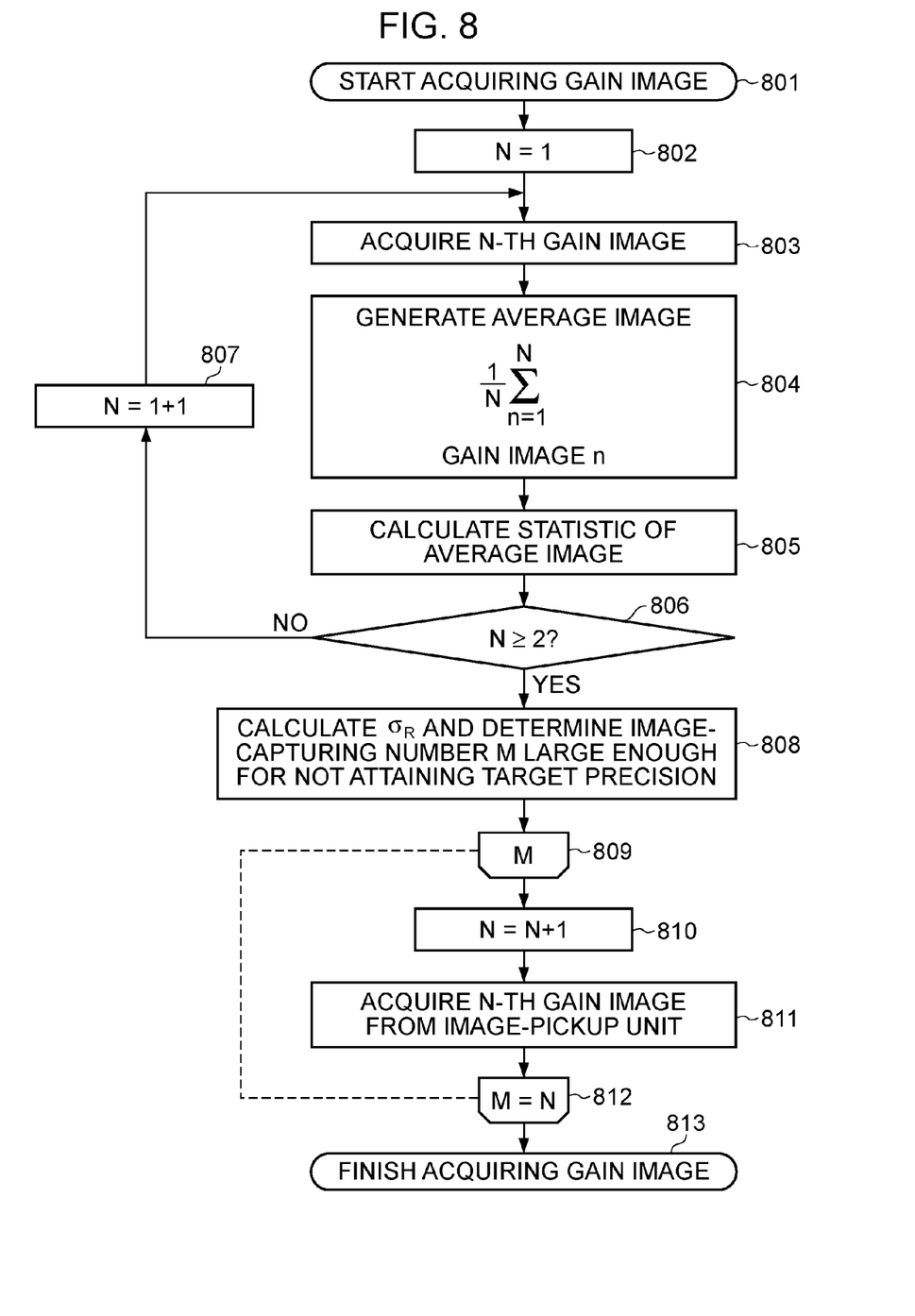
FIG. 8 is a flowchart of processing procedures performed to execute the third determining method.

FIG. 8 is a flowchart of processing procedures performed to attain the third determining method shown in FIG. 7. The details of the processing procedures will be described below. Here, the processing procedures corresponding to steps S801 to S805 of the third determining method are equivalent to those corresponding to steps S401 to S405 of the first determining method. Further, the processing corresponding to step S807 is equal to that corresponding to step S407.

Hereinafter, therefore, the processing procedures corresponding to step S806 and steps S808 to S813, which are different from the first determining method, will be described.

At step S806, the determining unit 105 determines whether the parameter N expressing the number of times the image capturing is performed denotes two. If the parameter N denotes two, it becomes possible to calculate the number of times the image capturing is performed, the number being large enough for not attaining the target precision. Therefore, the processing advances to step S808. If the parameter N does not denote two, it becomes difficult to calculate the number of times the image capturing is performed, the number being large enough for not attaining the target precision. Therefore, the processing advances to step S807.

At step S808, the image processing unit 201 calculates a standard deviation σR and determines an image-capturing number M which is large enough for not attaining the target precision. The standard deviation σR can be calculated according to Expression 704 shown in FIG. 7. As described above, the random-noise amount is decreased in order of $\sqrt{3}/3$, 1/2, and $\sqrt{5}/5$. Therefore, the above-described image-capturing number M can be calculated based on the standard deviation σR and the target precision.

At step S809, the determining unit 105 determines the image-capturing number M, which is large enough for not attaining the target precision, upon receiving data of the result of the processing performed by the image processing unit 201.

At step S810, the determining unit 105 adds one to the parameter N indicating the number of times the image capturing is performed. After the addition is performed, the processing advances to step S811.

At step S811, the image-capturing control unit 102 makes the radiation generator 101 emit radiation and acquires the N-th gain image.

At step S812, the determining unit 105 determines whether the parameter N indicating the number of times the image capturing is performed is equal to the image-capturing number M, which is large enough for not attaining the target precision. If the parameter N is equal to the image-capturing number M, it is determined that the image capturing is performed a number of times, where the number is large enough for not attaining the target precision, and the processing advances to step S813. If the parameter N is not equal to the image-capturing number M, it is determined that the above-described number is not large enough for not attaining the target precision, and the processing returns to step S809.

Since it is determined that the image capturing is performed the number of times at step S812, the number being large enough for not attaining the target precision, the radiographic apparatus stops acquiring the gain images at step S813.

Thus, the third determining method is executed by performing the above-described processing procedures. Through the use of the third determining method, the statistic may not be calculated every time the gain image is acquired, and processing can be performed with high speed.

(Fourth Determining Method)

Figure 9:
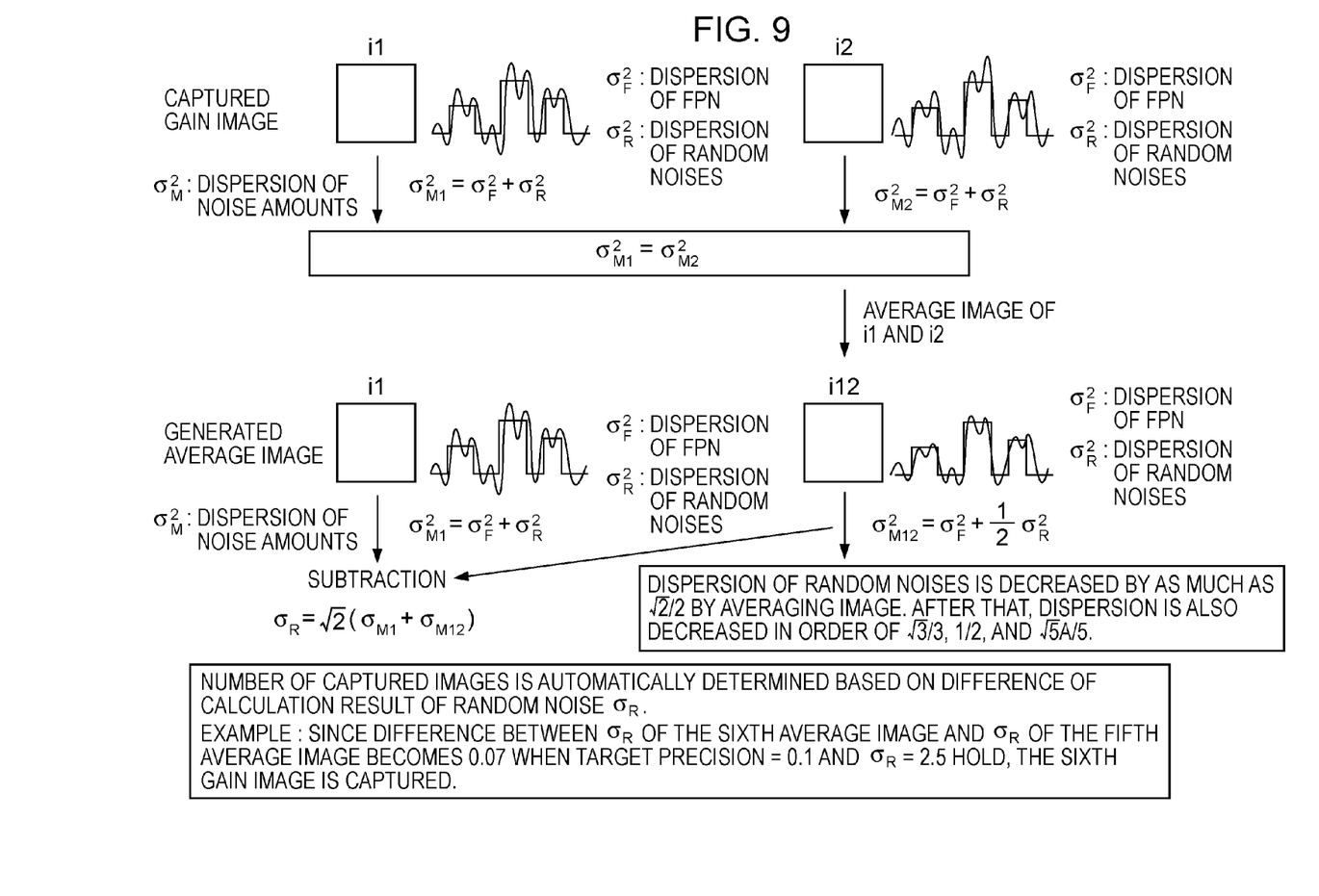
FIG. 9 shows a fourth determining method performed based on another target precision determined by the target-precision determining unit.

FIG. 9 shows the fourth determining method performed based on another target precision determined by the target-precision determining unit 202. The fourth determining method shown in FIG. 9 allows for calculating the dispersion of random noises, as is the case with the third determining method, and acquiring the gain images until the value of a calculated difference between the random noises falls below the target precision value.

Figure 10:
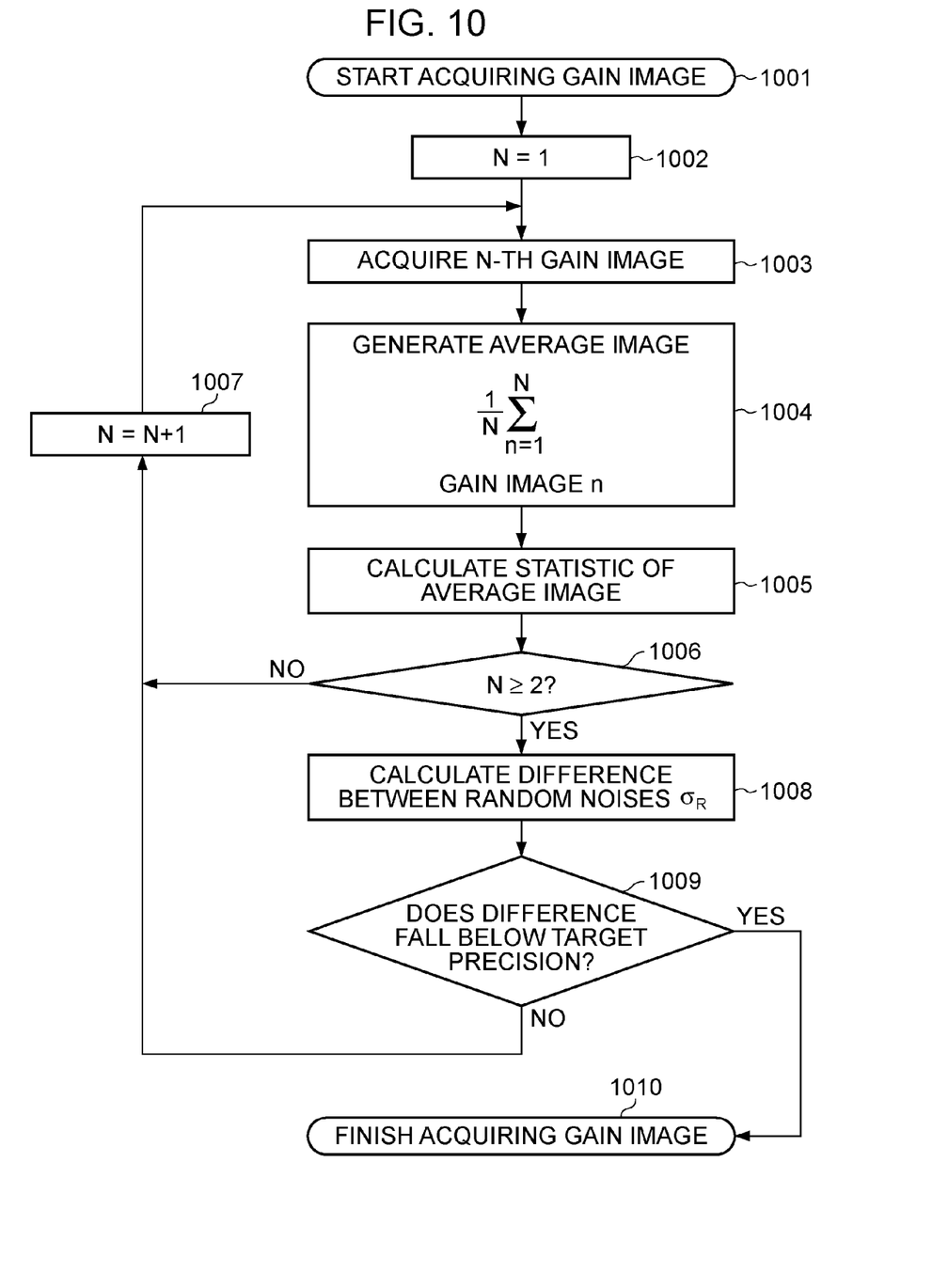
FIG. 10 is a flowchart of processing procedures performed to execute the fourth determining method.

FIG. 10 is a flowchart of processing procedures performed to execute the fourth determining method shown in FIG. 9. The details of the processing procedures will be described below. The processing procedures corresponding to steps S1001 to S1005 of the fourth determining method are equivalent to those corresponding to steps S401 to S405 of the first determining method. Further, the processing corresponding to step S1007 is equal to that corresponding to step S407.

Hereinafter, therefore, the processing procedures corresponding to step S1006 and steps S1008 to S1010, which are different from the first determining method, will be described.

At step S1006, the determining unit 105 determines whether the parameter N representing the number of times the image capturing is performed is equivalent to or greater than two. If the parameter N is equivalent to or greater than two, the standard deviation σR can be calculated. Therefore, the processing advances to step S1008. If the parameter N is not equivalent to or greater than two, it becomes difficult to calculate the standard deviation σR. Therefore, the processing advances to step S1007.

At step S1008, the image processing unit 201 calculates the difference in the standard deviation σR. The difference in the standard deviation σR can be calculated according to the method shown in FIG. 9.

At step S1009, the determining unit 105 determines whether the value of the difference calculated at step S1008 falls below the target precision value. If it is determined that the difference value falls below the target precision value, the processing advances to step S1010. Otherwise, the processing advances to step S1007.

At step S1010, the radiographic apparatus stops acquiring the gain images, since it is determined that the value of the difference calculated at step S1008 falls below the target precision value.

As described above, the use of the fourth determining method allows for performing the determining processing with precision higher than in the past.

Thus, according to the first and second embodiments, the number of times the correction image used to perform the calibration is captured is determined based on the image-capturing mode. Consequently, it becomes possible to reduce artifacts occurring in a captured and corrected image, and provide an image with high quality. Further, it becomes possible to determine the number of times the correction image used at the calibration time is captured appropriately and automatically, where the above-described time number has been determined by a user under empirical rule. Therefore, it becomes possible to eliminate users having to make settings and reduce unnecessary radiography, so that the users are exposed to less radiation and the life of the radiation source (X-ray tube) is increased.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

What is claimed is:

1. A radiography control apparatus comprising:
   an acquisition unit configured to acquire a radiographic image and a correction image which is used to correct the radiographic image;
   an analyzing unit configured to analyze a statistic of the correction image; and
   a control unit configured to control the acquisition unit to acquire the correction image until the statistic value analyzed by the analyzing unit reaches a target value.

2. The radiography control apparatus according to claim 1, wherein the control unit is configured to control the acquisition of the correction image based on whether the statistic indicating at least one random noise of the correction image reaches a target value.

3. The radiography control apparatus according to claim 2, wherein the control unit controls the acquisition unit to acquire the correction image until the statistic value reaches the target value.

4. The radiography control apparatus according to claim 2, wherein the control unit controls the acquisition unit to acquire the correction image until the statistic value calculated based on an average image of a plurality of the correction images reaches the target value.

5. The radiography control apparatus according to claim 2, wherein if the statistic value falls below the target value, the acquisition of the correction image is terminated.

6. The radiography control apparatus according to claim 2, wherein a control unit is configured to control the acquisition of the correction image based on comparison between the statistic of the average image of the acquired correction images and the target value.

7. The radiography control apparatus according to claim 2, wherein a control unit configured to control an acquisition of the correction image based on comparison between a difference value of the statistic of the average image of the acquired correction images and the target value.

8. The radiography control apparatus according to claim 2, wherein a control unit configured to control an acquisition of the correction image based on dispersion of random noises or difference between the random noises occurring in the correction image.

9. The radiography control apparatus according to claim 1, wherein the statistic is a standard deviation or dispersion of a distribution of pixel values of the correction image.

10. A radiography control method comprising:
    acquiring a radiographic image and a correction image which is used to correct the radiographic image;
    analyzing a statistic of the correction image; and
    controlling an acquisition of the correction image until the statistic value analyzed by the analyzing reaches a target value.

11. The radiography control method according to claim 10, wherein the controlling controls the acquisition of the correction image based on whether the statistic indicating at least one random noise of the correction image reaches a target value.

12. The radiography control method according to claim 11, wherein the controlling controls the acquiring to acquire the correction image until the statistic value reaches the target value.

13. The radiography control method according to claim 11, wherein the controlling controls the acquiring to acquire the correction image until the statistic value calculated based on an average image of a plurality of the correction images reaches the target value.

14. The radiography control method according to claim 11, wherein if the statistic value falls below the target value, the acquisition of the correction image is terminated.

15. The radiography control method according to claim 11, wherein a controlling controls the acquisition of the correction image based on comparison between the statistic of the average image of the acquired correction images and the target value.

16. The radiography control method according to claim 11, wherein a controlling controls an acquisition of the correction image based on comparison between a difference value of the statistic of the average image of the acquired correction images and the target value.

17. The radiography control method according to claim 11, wherein a controlling controls an acquisition of the correction image based on dispersion of random noises or difference between the random noises occurring in the correction image.

18. The radiography control method according to claim 10, wherein the statistic is a standard deviation or dispersion of a distribution of pixel values of the correction image.

19. A non-transitory computer readable medium storing a computer-executable program of instructions for causing a computer to perform a radiography control method comprising:
    acquiring a radiographic image and a correction image which is used to correct the radiographic image;
    analyzing a statistic of the correction image; and
    controlling an acquisition of the correction image until the statistic value analyzed by the analyzing reaches a target value.

20. The non-transitory computer readable medium according to claim 19, wherein the controlling controls the acquisition of the correction image based on whether the statistic indicating at least one random noise of the correction image reaches a target value.

21. The non-transitory computer readable medium according to claim 20, wherein the controlling controls the acquiring to acquire the correction image until the statistic value reaches the target value.

22. The non-transitory computer readable medium according to claim 20, wherein the controlling controls the acquiring to acquire the correction image until the statistic value calculated based on an average image of a plurality of the correction images reaches the target value.

23. The non-transitory computer readable medium according to claim 20,
    wherein if the statistic value falls below the target value, the acquisition of the correction image is terminated.

24. The non-transitory computer readable medium according to claim 20, wherein a controlling controls the acquisition of the correction image based on comparison between the statistic of the average image of the acquired correction images and the target value.

25. The non-transitory computer readable medium according to claim 20, wherein a controlling controls an acquisition of the correction image based on comparison between a difference value of the statistic of the average image of the acquired correction images and the target value.

26. The non-transitory computer readable medium according to claim 20, wherein a controlling controls an acquisition of the correction image based on dispersion of random noises or difference between the random noises occurring in the correction image.

27. The non-transitory computer readable medium according to claim 19, wherein the statistic is a standard deviation or dispersion of a distribution of pixel values of the correction image.

* * * * *